US009145361B2

(12) United States Patent  
Gee et al.

(10) Patent No.: US 9,145,361 B2  
(45) Date of Patent: Sep. 29, 2015

(54) SDP-CONTAINING HETEROBIFUNCTIONAL AGENTS

(75) Inventors: Kyle Gee, Springfield, OR (US); Aimei Chen, Eugene, OR (US); Hee Chol Kang, Eugene, OR (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/006,129

(22) PCT Filed: Mar. 22, 2012

(86) PCT No.: PCT/US2012/030031  
§ 371 (c)(1),  
(2), (4) Date: Nov. 6, 2013

(87) PCT Pub. No.: WO2012/134925  
PCT Pub. Date: Oct. 4, 2012

(65) Prior Publication Data  
US 2014/0107323 A1    Apr. 17, 2014

Related U.S. Application Data

(60) Provisional application No. 61/467,674, filed on Mar. 25, 2011.

(51) Int. Cl.
| | |
|---|---|
| *G01N 33/532* | (2006.01) |
| *C07C 309/42* | (2006.01) |
| *C07D 225/02* | (2006.01) |
| *C07D 225/08* | (2006.01) |
| *C07K 16/18* | (2006.01) |
| *C07D 223/08* | (2006.01) |
| *C07D 223/26* | (2006.01) |
| *C07K 1/13* | (2006.01) |

(52) U.S. Cl.  
CPC ............ *C07C 309/42* (2013.01); *C07D 223/08* (2013.01); *C07D 223/26* (2013.01); *C07D 225/02* (2013.01); *C07D 225/08* (2013.01); *C07K 1/13* (2013.01); *C07K 16/18* (2013.01); *G01N 33/532* (2013.01); *C07C 2103/36* (2013.01)

(58) Field of Classification Search  
CPC . G01N 33/532; C07C 2103/36; C07C 309/42  
See application file for complete search history.

(56) References Cited

U.S. PATENT DOCUMENTS

2009/0004753 A1*   1/2009   Antoulinakis et al. ........ 436/166

FOREIGN PATENT DOCUMENTS

WO    WO-2009067663    5/2009

OTHER PUBLICATIONS

"Alexa Fluor 488 5-SDP Ester; product A30052", *Life Technologies*, XP002678892 http://products.invitrogen.com/ivgn/product/A30052.

"Click Chemistry", Section 3.1, *Molecular Probes: The Handbook*, XP002678889 http://web.archive.org/web/20100812095456/http://www.invitrogen.com/site/us/en/home/References/Molecular-Probes-The-Handbook/Reagents-for-Modifying-Groups-Other-Than-Thiols-or-Amines/Click-Chemistry, Aug. 12, 2010.

"Introduction to Amine Modification", Section 1.1, *Sulfodichlorophenol (SDP) Esters, Molecular Probes: The Handbook*, XP002678888 http://web.archive.org/web/20100420095611/http://www.invitrogen.com/site/us/en/home/References/Molecular-Probes-The-Handbook/Fluorophores-and-Their-Anmine-Reactive-, Apr. 20, 2010.

"Product Structure A10279", *Life Technologies*, XP002678890 http://www.invitrogen.com/site/us/en/home/support/Product-Technical-Resources/Product- Structures.-10279.

"Product Structure A10280", *Life Technologies*, XP002678891 http://www.invitrogen.com/site/us/en/home/support/Product-Technical-Resources/Product-Structures.-10280.html.

Hong, Vu et al., "Analysis and Optimization of Copper-Catalyzed Azide-Alkyne Cycloaddition for Bioconjugation", *Angew. Chem. Inst. Ed.*, 48, 2009, 9879-9883.

PCT/US2012/030031, , "International Search Report", 2012, 6 pgs.

Sletten, E et al., "A Hydrophilic Azacyclooctyne for Cu-Free Click Chemistry", *Organic Letters*, vol. 10(14), 2008, pp. 3097-3099.

Sletten, Ellen et al., "Supporting Information for: A hydrophilic azacyclooctyne for Cu-free click chemistry", XP55031304; http:/pubs.acs.org/doi/suppl/10.1021/ol801141k/suppl_file/ol801141k-file002.pdf, 2008, S1-S35.

* cited by examiner

*Primary Examiner* — Erich A Leeser  
(74) *Attorney, Agent, or Firm* — Life Technologies Corporation

(57) ABSTRACT

The present disclosure is directed to a reactive ester agent for conjugating a click-reactive group to a carrier molecule or solid support. The reactive ester agent has the general formula IA, wherein the variables $R^1$, $R^2$, $R^3$, $R^a$ and L are described throughout the application.

19 Claims, 3 Drawing Sheets

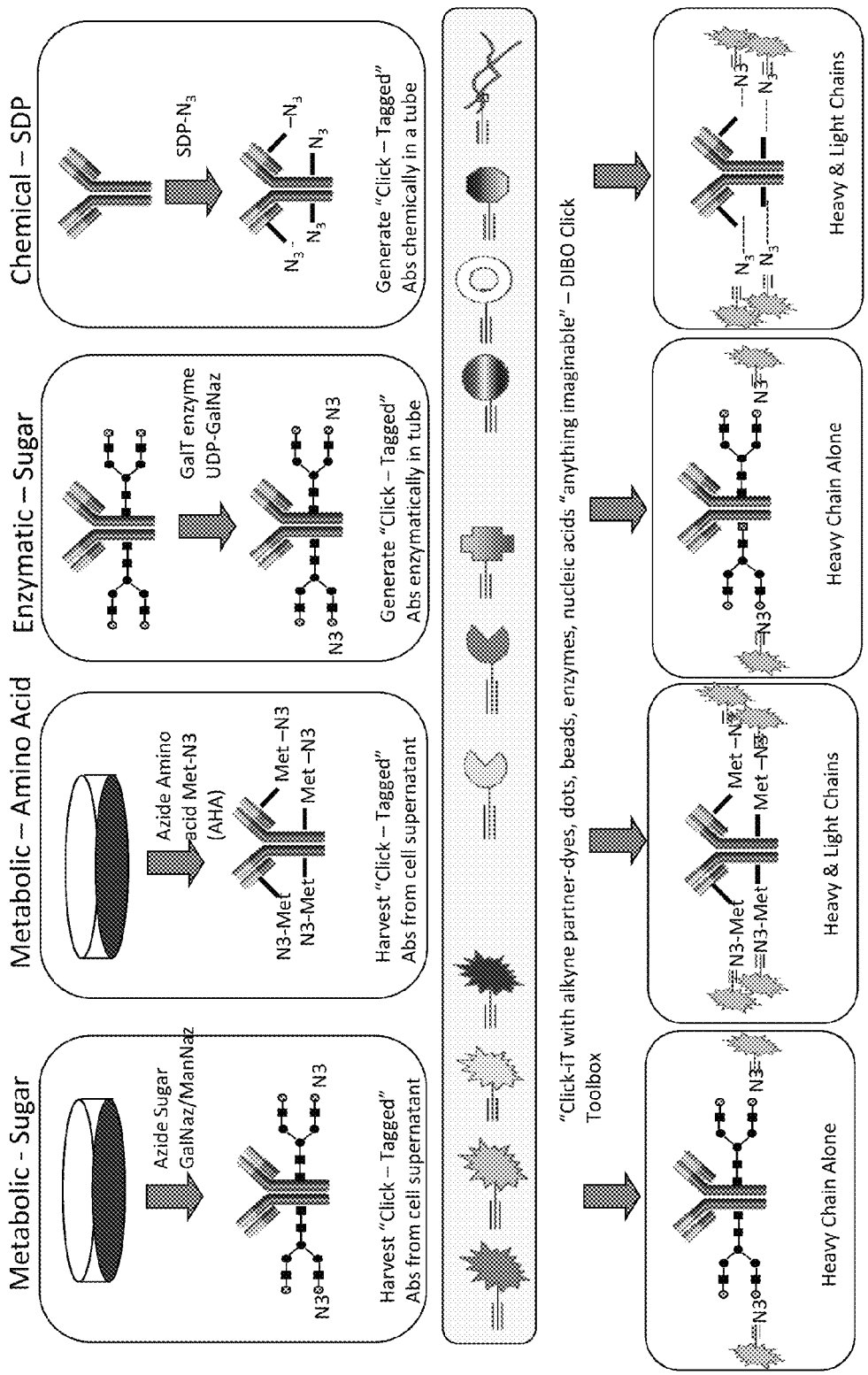

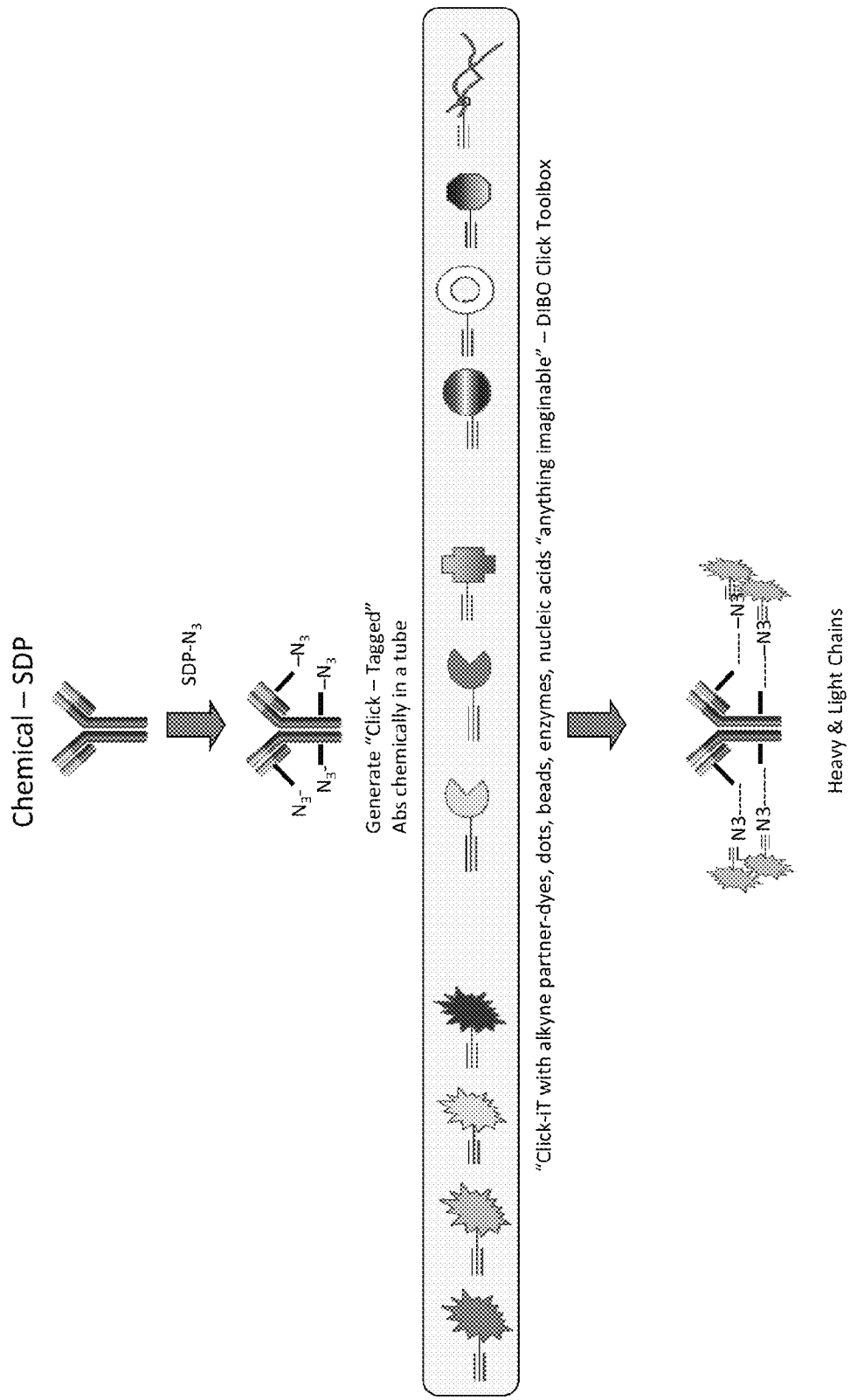

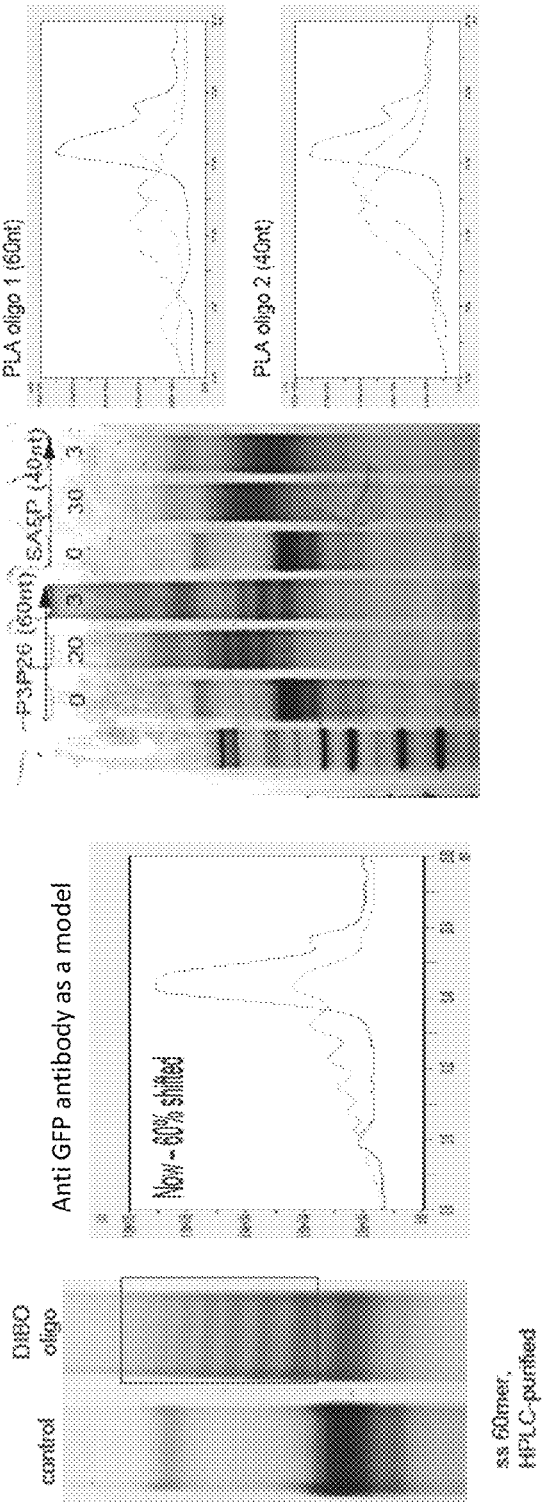

SDP-CONTAINING HETEROBIFUNCTIONAL AGENTS

This application is a 371 National Stage Application of International Application Serial No. PCT/US2012/030031, which claims priority to U.S. provisional patent application No. 61/467,674 filed Mar. 25, 2011, the disclosures of which are incorporated by reference in their entirety.

FIELD OF THE INVENTION

Novel click-reactive compounds and methods of labeling are disclosed. The compounds are activated with water solubalizing phenolic esters and contacted with a carrier molecule or solid support comprising a nucleophile to yield a click-labeled carrier molecule or solid support.

BACKGROUND OF THE INVENTION

The ability to effectively click-label a target molecule is dependent on the reactive groups present on both the label and target molecule in the reaction and the conjugation conditions. Reagents such as succinimidyl esters (SE) and perfluorophenyl (PFP) esters have high reactivity rates with water, thereby limiting preparation, packaging, dispensing and purification conditions and their subsequent shelf life. In addition, due to their hydrolytic reactivity, most of the reagents used in a biomolecule labeling reaction in aqueous buffers hydrolyze prior to reaction with the desired biomolecule; therefore, such reagents are largely wasted (often necessitating their use in molar excess).

Gee et al. (Tetrahedron Letters (1999), 40, 1471-1474) describes 4-sulfotetrafluorophenyl (STP) esters for use in dye labeling. These groups have been shown to be amenable to conjugation in aqueous environments.

Koichi et al. (Chemical & Pharmaceutical Bulletin (1987), 35(3), 1044-1048) and Tsuji et al. (Peptide Chemistry (1986), Volume Date 1985, 23rd 111-114) describe peptide synthesis via ester activation with potassium dichlorophenolsulfonate, sodium dibromophenolsulfonate, and sodium nitrophenolsulfonate. No description of labeling or conjugation of molecules is provided.

While many labeling reagents exist and have been used with intermittent success, there remains a need for click-labeling reagents that produce high labeling yields under biologically relevant reaction conditions. Additionally, a need exists for click-labeling reagents that are stable and do not hydrolyze in aqueous environments.

SUMMARY OF THE INVENTION

The present invention provides a reactive group, which has greater hydrolytic stability than standard N-hydroxysuccinimidyl (SE) and perfluorophenolic (PFP) esters, that when attached via an intervening linker to a click-reactive group forms a click-labeling reagent of the present invention. The reactive group of the present invention is water soluble and yields a click-labeling reagent with exceptional aqueous stability.

One illustrative aspect of the present invention provides a compound of Formula IA or a salt thereof:

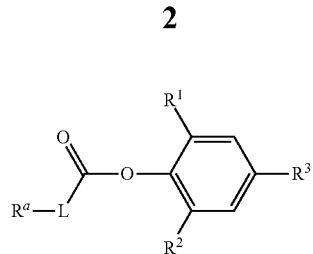

wherein
L is a linker,
$R^1$ is a halogen,
$R^2$ is a halogen,
$R^3$ comprises a water solubilizing group, and
$R^a$ is a click-reactive group.

Another illustrative aspect of the present invention provides a method of making a compound of Formula IA or a salt thereof:

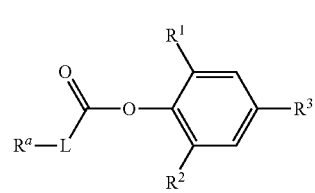

said method comprising:
contacting a compound of Formula IB or a salt thereof:

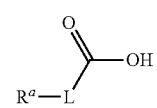

with a compound of Formula IC or a tautomer or salt thereof:

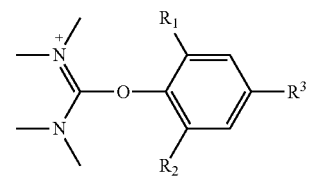

wherein
$R^1$ is a halogen,
$R^2$ is a halogen,
$R^3$ comprises a water solubilizing group,
L is a linker, and
$R^a$ is a click-reactive group.

Another illustrative aspect of the present invention provides a method of click-labeling a carrier molecule or solid support, said method comprising:
contacting said carrier molecule or solid support comprising a nucleophilic group X and having the formula $R^b$—X with a compound of Formula IA or a salt thereof:

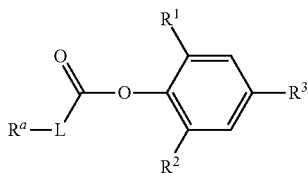

wherein
L is a linker,
$R^1$ is a halogen,
$R^2$ is a halogen,
$R^3$ comprises a water solubilizing group, and
$R^a$ is a click-reactive group;
and
forming a compound of Formula I or a salt thereof:

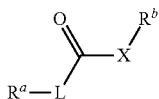

wherein
L is the linker,
$R^a$ is the click-reactive group, and
$R^b$ is the carrier molecule or solid support comprising the nucleophilic group X.

Another illustrative aspect of the present invention provides a click-labeled carrier molecule or solid support having the formula:

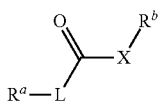

wherein
L is a linker,
$R^a$ is a click-reactive group, and
$R^b$ is a carrier molecule or solid support comprising nucleophilic group X.

Another illustrative aspect of the present invention provides a kit for click-labeling a carrier molecule or solid support, wherein said kit comprises:
a) a compound of Formula IA or a salt thereof:

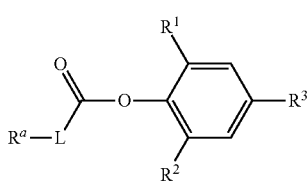

wherein
L is a linker,
$R^1$ is a halogen,
$R^2$ is a halogen,
$R^3$ comprises a water solubilizing group, and
$R^a$ is a click-reactive group;
and
b) instructions for click-labeling the carrier molecule or solid support.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 shows Click Antibody—Multiple Tagging Concepts: Addition of azide groups to antibody heavy and/or light chains via different routes: Metabolic-Sugar, Metabolic-Amino Acid, Enzymatic-Sugar, and Chemical-SDP.

FIG. 2 shows Click Antibody—Tagging Click Handle Chemically: Use of SDP-$N_3$ to chemically click-label antibody heavy and light chains with azide groups enables subsequent click-chemistry.

FIG. 3 shows Chemical (SDP-$N_3$) Click Tagging—A Very Efficient Process: Chemical click-labeling using SDP-$N_3$ to label amino group side chains of Lys residues in anti-GFP antibody; labeling is not chain specific and is dictated by the frequency of Lys residues (SDP-$N_3$-Modified Antibody+ DIBO converted Oligo shown).

DETAILED DESCRIPTION OF THE INVENTION

The present invention provides click-labeling reagents for click-labeling carrier molecules or solid supports. The click-labeling reagents of the present invention generally include a compound of Formula IA, comprising a phenolic ester for activation of a click-reactive group, wherein L is a linker, $R^1$ is a halogen, $R^2$ is a halogen, $R^3$ comprises a water solubilizing group, and $R^a$ is a click-reactive group:

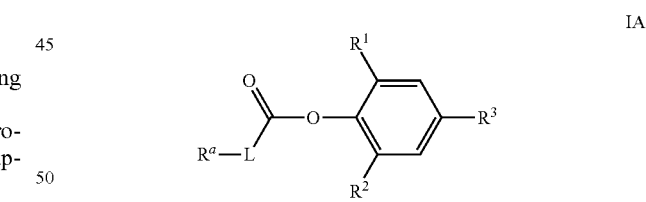

After activation of a click-reactive group, the resulting click-labeling reagent is contacted with a carrier molecule or solid support comprising at least one nucleophilic group, such as an amine, thiol or hydroxyl group, whereupon a click-labeled carrier molecule or solid support is formed. The resulting click-labeled carrier molecule, for example, is stable, thereby providing an excellent method for click-labeling a biomolecule such as a protein or polynucleotide. The resultant biomolecule can subsequently be added to a biological solution for use in a number of click-type cycloaddition reactions including, but not limited to, i) copper-catalyzed Huisgen cycloaddition or the 1,3-dipolar cycloaddition between an azide and a terminal alkyne to form a 1,2,4-triazole, ii) a Diels-Alder reaction, which is a cycloaddition reaction between a diene and a dienophile, and/or iii) nucleophilic substitution reactions in which one of the reactive species is an epoxy or aziridine compound with significant ring strain.

The phenolic esters described herein have excellent stability properties in aqueous solutions and retain a high degree of reactivity for amines on biomolecules, making them ideal choices as components of the click-labeling reagents of the present invention. Their hydrolytic stability has significant impact on the preparation, ease of handling, storage stability, and biomolecule labeling efficiency. Additionally, with use of the click-labeling reagents of the present invention, purification of the reagents is significantly improved and can be done by silica gel flash chromatography. Column purification is not possible with many conventional SE or PFP esters, due to the high reactivity and low stability of the molecules. The esters of the present invention are also stable to lyophylization which greatly increases the ease of handling and packaging. With greater hydrolytic stability also comes less degradation upon storage than that for existing ester-modified labeling reagents, such as SE and PFP esters.

In addition, greater hydrolytic stability affords greater labeling efficiency, with compounds of the present invention giving nearly twice as much biomolecule labeling as an equivalent amount of SE. Without being bound to theory, it is believed that this effect is also due, at least in part, to a molecular scenario in which, for example, an SDP moiety "guides" a click-labeling reagent of the present invention to more and/or better site(s) on a carrier molecule or solid support than does an SE or PFP moiety.

Furthermore, the compounds of the present invention have been shown to be active to biomolecular labeling under a wide range of pH conditions, from pH 6-9. A wide pH reactivity range is an important characteristic since many biomolecules are unable to be labeled at higher pH due to their limited solubility. This is also advantageous in the selective N-terminal labeling of proteins which generally occurs at a lower pH range.

DEFINITIONS

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. Thus, for example, reference to "a click-reactive group" includes a plurality of such groups, and reference to "a linker" includes a plurality of linkers, and so on and so forth.

Unless defined otherwise, all technical and scientific terms used herein have the same meaning as commonly understood by one of ordinary skill in the art to which this invention is related. The following terms are defined for purposes of the invention as described herein:

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkyne reactive," as used herein, refers to a chemical moiety that selectively reacts with an alkyne modified group on another molecule to form a covalent chemical bond between the alkyne modified group and the alkyne reactive group. Examples of alkyne-reactive groups include, but are not limited to, azides. "Alkyne-reactive" can also refer to a molecule that contains a chemical moiety that selectively reacts with an alkyne group.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —$SO_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—$SO_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

The term "aqueous solution," as used herein, refers to a solution that is predominantly water and retains the solution characteristics of water. Where the aqueous solution contains solvents in addition to water, water is typically the predominant solvent.

The term "azide reactive," as used herein, refers to a chemical moiety that selectively reacts with an azido modified group on another molecule to form a covalent chemical bond between the azido modified group and the azide reactive group. Examples of azide-reactive groups include, but are not limited to, alkyne, including, but not limited to terminal alkynes; phosphines, including, but not limited to, triarylphosphines; and cyclooctynes and difluorocyclooctynes as described by Agard et al., J. Am. Chem. Soc., 2004, 126 (46):15046-15047, dibenzocyclooctynes as described by Boon et al., WO2009/067663 A1 (2009), and aza-dibenzocyclooctynes as described by Debets et al., Chem. Comm., 2010, 46:97-99. The various dibenzocyclooctynes described above are collectively referred to herein as cyclooctyne groups. "Azide-reactive" can also refer to a molecule that contains a chemical moiety that selectively reacts with an azido group.

"Azenyl" refers to the group —N=NH. "Substituted azenyl" refers to —N=NR', wherein R' is alkyl, substituted alkyl, amino (i.e. triazenyl), imino(azide), substituted amino, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, or a substituted heterocyclic group.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"DIBO" refers to dibenzocyclooctyne.

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$—, =NNH—, or =N$^{(+)}$HNH$_2$—.

The term "kit," as used herein, refers to a packaged set of related components, typically one or more compounds or compositions, and instructions for use thereof.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$(alkyl)-NH$_2$.

"Nitro" refers to the group —NO$_2$.

"Oxo" refers to the atom (=O) or (—O$^-$).

The term "SDP," as used herein refers to sulfodichlorophenol and to sulfodichlorophenyl when referring to an ester.

"SDP-N$_3$," as used herein, refers to the compound:

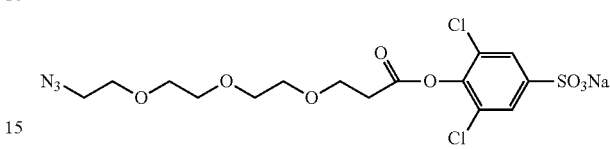

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

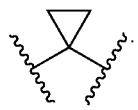

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moeity such as pyrazoles, imidazoles, benzimidazoles, triazoles, and tetrazoles.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

A "water solubilizing group" as used herein indicates a polar and/or charged, preferably anionic, substituent that increases water solubility of a base molecule. Water solubilizing groups may be appended directly to the base molecule, or through a linker. Water solubilizing groups of the present invention include carboxyl groups, sulphonic acids, hydroxyl groups, substituted azenyl groups, polyoxyalkylene (such as PEG), phosphate groups, bisphosphonate groups, or substitutions that introduce an additional net charge and/or polarity into the molecule.

The term "reactive group" as used herein refers to a group that is capable of reacting with another chemical group to form a covalent bond, i.e. is covalently reactive under suitable reaction conditions, and generally represents a point of attachment for another substance. In the present invention the labeling reagents comprise a reactive group according to Formula IA and the carrier molecule or solid support comprises at least one suitable nucleophile that will react with the reactive group according to Formula IA to form a covalent bond.

The term "carrier molecule" as used herein refers to a biological or a non-biological component that can be covalently bonded to a labeling reagent of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. As used herein carrier molecules comprise a nucleophile for reaction with the present labeling reagents. Carrier molecules are described in greater detail below.

The term "click-reactive group," as used herein, refers to a chemical moiety that is reactive in, for example, i) copper-catalyzed Huisgen cycloaddition or the 1,3-dipolar cycloaddition between an azide and a terminal alkyne to form a 1,2,4-triazole, ii) a Diels-Alder reaction, which is a cycloaddition reaction between a diene and a dienophile, and/or iii) nucleophilic substitution reactions in which one of the reactive species is an epoxy or aziridine compound with significant ring strain. Such chemical reactions can use, but are not limited to, simple heteroatomic organic reactants and are reliable, selective, stereospecific, and exothermic. Compounds of the present invention, which compounds include a "click-reactive group," are not limited to those requiring copper-catalysis for use in cycloaddition. Any clickable compound capable of carrying an SDP group is regarded as being within the scope of the present invention.

"Covalently bonded" as used herein indicates a direct covalent linkage or through a number of atoms corresponding to a linker moiety.

The term "cycloaddition" as used herein refers to a chemical reaction in which two or more π (pi)-electron systems (e.g., unsaturated molecules or unsaturated parts of the same molecule) combine to form a cyclic product in which there is a net reduction of the bond multiplicity. In a cycloaddition, the π (pi) electrons are used to form new π (pi) bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 1,3-dipolar cycloadditions, occur between a 1,3-dipole and a dipolarophile and are typically used for the construction of five-membered heterocyclic rings. The term "[3+2] cycloaddition" also encompasses "copperless" [3+2] cycloadditions between azides and cyclooctynes and difluorocyclooctynes described by Agard et al., J. Am. Chem. Soc., 2004, 126 (46):15046-15047, the dibenzocyclooctynes described by Boon et al., WO2009/067663 A1 (2009), and the aza-dibenzocyclooctynes described by Debets et al., Chem. Comm., 2010, 46:97-99.

The term "Labeling Reagent" as used herein refers to present compound that comprises a click-reactive group and a phenolic ester according Formula IA.

The term "Linker" as used herein, refers to a single covalent bond or a series of stable covalent bonds incorporating 1-20 nonhydrogen atoms selected from the group consisting of C, N, O, S and P. The present labeling reagent may comprise a linker that covalently attaches the reporter molecule to the reactive group according to Formula IA or to a carrier group or solid support. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The term "sample" as used herein refers to any material that may contain an analyte of interest, as defined below, or a carrier molecule or solid support of the present invention. Typically, the sample comprises a population of cells, cellular extract, subcellular components, tissue culture, a bodily fluid, and tissue. The sample may be in an aqueous solution, a viable cell culture or immobilized on a solid or semi solid surface such as a gel, a membrane, a glass surface, a microparticle or on a microarray.

The term "solid support" as used here refers to a matrix or media that is substantially insoluble in liquid phases and capable of binding a molecule or particle of interest. Solid supports of the current invention include semi-solid supports and are not limited to a specific type of support. Useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

Click-Labeling Reagents

In accordance with the present invention, click-labeling reagents, as well as methods for labeling carrier molecules in a sample or labeling a solid support with such reagents, are provided. The click-labeling reagents of the present invention comprise a click-reactive group, as defined herein, and a reactive phenolic ester according to Formula IA, as defined herein. The click-labeling reagents may be used to label a wide variety of carrier molecules and solid supports by methods well known in the art, which labeled carrier molecules and solid supports may then be used in a variety of click-type cycloaddition reactions including, but not limited to i) copper-catalyzed Huisgen cycloaddition or the 1,3-dipolar cycloaddition between an azide and a terminal alkyne to form a 1,2,4-triazole, ii) a Diels-Alder reaction, which is a cycloaddition reaction between a diene and a dienophile, and/or iii) nucleophilic substitution reactions in which one of the reactive species is an epoxy or aziridine compound with significant ring strain. Compounds of the present invention, which compounds include a "click-reactive group," are not limited to those requiring copper-catalysis for use in cycloaddition. Any clickable compound capable of carrying an SDP group is regarded as being within the scope of the present invention.

One illustrative aspect of the present invention provides a compound of Formula IA or a salt thereof:

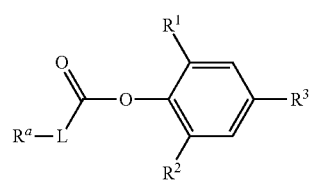

IA wherein
L is a linker,
$R^1$ is a halogen,
$R^2$ is a halogen,
$R^3$ comprises a water solubilizing group, and
$R^a$ is a click-reactive group.

In one embodiment, L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -alkoxyalkyl-, poly(alkoxyalkyl)-, PEG, -thio-, -amino-, or -substituted amino-. More particular still, L is single a covalent bond. Alternatively, L is -alkyl- or -substituted alkyl-; more particularly -pentyl- or -polyethylglycol- or -amino-dPEG$_4$-acid. Alternatively, L is -substituted heterocyclyl-; more particularly, -piperidine-1-carbonyl-.

In another embodiment, $R^1$ and $R^2$ are chloro. In another embodiment, $R^1$ and $R^2$ are fluoro.

In another embodiment, $R^3$ is —COO$^-$, —SO$_3^-$, substituted azenyl, PEG, phosphate, or bisphosphonate. More particularly, $R^3$ is —SO$_3^-$.

In a particularly preferred embodiment, $R^1$ and $R^2$ are chloro and $R^3$ is —SO$_3^-$.

In another embodiment, $R^a$ is an alkyne reactive moiety, an azide reactive moiety, a diene, a dienophile, an epoxide, or an aziridine compound. In another embodiment, the click-reactivity of $R^a$ is copper-catalyzed. In yet another embodiment, the click-reactivity of $R^a$ is not copper-catalyzed. More particularly, $R^a$ is an alkyne reactive moiety or an azide reactive moiety.

In another embodiment, the compound of Formula IA is a salt. More particularly, the salt comprises a potassium ion, a sodium ion, or a triethylammonium ion.

In another embodiment, the compound of Formula IA is soluble in an aqueous solution.

In another embodiment, the compound of Formula IA has the formula:

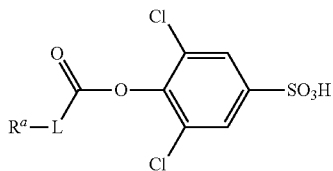

or salt thereof,
wherein
L is a linker and $R^a$ is a click-reactive group.

In yet another embodiment, a compound of the present invention has the formula:

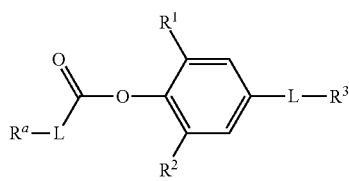

wherein the variables are as described herein, and each L group is independent of the other.

Another illustrative aspect of the present invention provides a method of making a compound of Formula IA or a salt thereof:

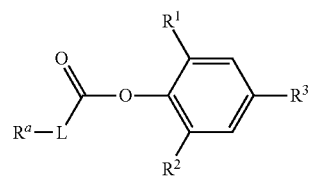

said method comprising:
contacting a compound of Formula IB or a salt thereof:

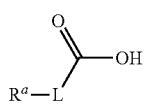

with a uronium salt compound of Formula IC or a tautomer or salt thereof:

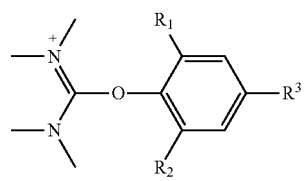

wherein
$R^1$ is a halogen,
$R^2$ is a halogen,
$R^3$ comprises a water solubilizing group,
L is a linker, and
$R^a$ is a click-reactive group.

In a particular embodiment, the contacting step is done in the presence of dimethylaminopyridine (DMAP). In another embodiment, the contacting step is done in an organic solvent.

Another illustrative aspect of the invention provides a uronium salt compound having the following structure or a tautomer or salt thereof:

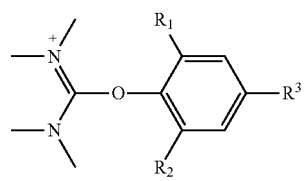

wherein
$R^1$ is a halogen,
$R^2$ is a halogen, and
$R^3$ is a water solubilizing group.

In one embodiment, $R^1$ and $R^2$ are chloro. In another embodiment, $R^3$ is $-SO_3^-$. In a particularly preferred embodiment, $R^1$ and $R^2$ are chloro and $R^3$ is $-SO_3$.

In general, click-labeling reagents (compounds) of the present invention of Formula IA are prepared by condensation of a phenol of the formula:

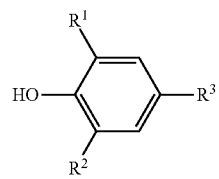

wherein $R^1$, $R^2$, and $R^3$ are as defined herein, with a click-reactive group $R^a$ that contains a carboxylic acid and a linker, wherein $R^a$ and L are as defined herein, in organic or aqueous/organic solvent systems. The carboxylic acid can be activated in situ with a reagent such as a carbodiimide, followed by reaction with the phenol XI. The carboxylic acid can also be activated by conversion to an electrophilic equivalent such as an acid chloride, followed by reaction with the phenol XI.

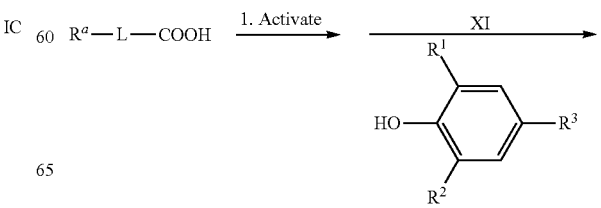

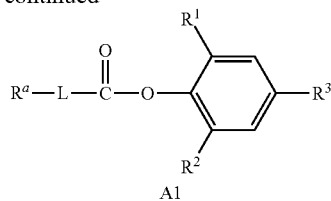

Alternatively, the phenol XI can be activated by conversion into a uronium salt, either preparatively or in situ, followed by reaction with a carboxylic acid; this reaction can be facilitated by a catalyst such as 4-dimethylaminopyridine (DMAP):

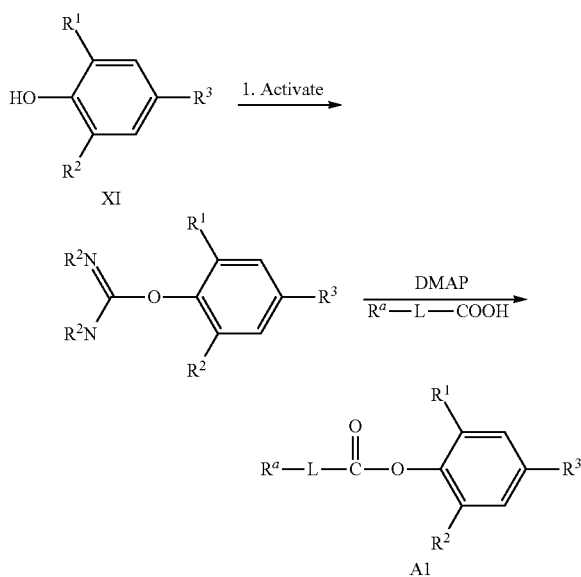

The click-labeling reagents may be used to click-label a wide variety of carrier molecules and solid supports by methods well known in the art, which labeled carrier molecules and solid supports may then be used in a variety of click-type cycloaddition reactions. The solid support or carrier molecule may be directly attached (where Linker is a single bond) to click-labeling reagents or attached through a linker, i.e., a series of stable bonds. When the linker is a series of stable covalent bonds the linker typically incorporates 1-30 nonhydrogen atoms selected from the group consisting of C, N, O, S and P. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and is composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, or arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —$(CH_2)_d(CONH(CH_2)_e)_z$— or where d is an integer from 0-5, e is an integer from 1-5 and z is 0 or 1. In a further embodiment, the linker is or incorporates the formula —O—$(CH_2)$—. In yet another embodiment, the linker is or incorporates a phenylene or a 2-carboxy-substituted phenylene.

In a preferred embodiment, any one of the aforementioned click-labeling reagents (compounds) is used in the methods described below.

Preparation of Conjugates

In another illustrative embodiment is provided a method for forming conjugates of the present click-labeling reagents and a carrier molecule or solid support. This method comprises:

a) combining a click-labeling reagent of the present invention with a carrier molecule or solid support to form a combined sample, wherein the reagent is a compound of Formula IA; and, b) incubating the combined sample for a sufficient amount of time for the compound to form a covalent bond with either the carrier molecule or solid support whereby a conjugate is formed.

Conjugates of carrier molecules, e.g., drugs, peptides, toxins, nucleotides, phospholipids and other organic molecules, as well as conjugates of solid supports are prepared by organic synthesis methods well recognized in the art (Haugland, MOLECULAR PROBES, supra, (2005)) using the click-labeling reagents of the invention. Preferably, conjugation to form a covalent bond consists of simply mixing the click-labeling reagents of the present invention in a suitable solvent in which both the reagents and the substance to be conjugated are soluble. The reaction preferably proceeds spontaneously without additional reagents at room temperature or below. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the compounds of the present invention.

Preparation of peptide or protein conjugates typically comprises first dissolving the peptide or protein to be conjugated in aqueous buffer at about 1-10 mg/mL at room temperature or below. The appropriate click-labeling reagent is then dissolved in a nonhydroxylic solvent (usually DMSO or DMF) in an amount sufficient to give a suitable degree of conjugation when added to a solution of the protein to be conjugated. The appropriate amount of reagent for any protein or other component is conveniently predetermined by experimentation in which variable amounts of the reagent are added to the protein, the conjugate is chromatographically purified to separate unconjugated compound and the click-labeled protein conjugate is tested in its desired application.

Following addition of the click-labeling reagent to the component solution, the mixture is incubated for a suitable period (typically about 1 hour at room temperature to several hours on ice), and excess reagent is removed by gel filtration, dialysis, HPLC, adsorption on an ion exchange or hydrophobic polymer or other suitable means. The click-labeled-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides) or multiple types of reactive sites (e.g. amines, thiols, alcohols, phenols) may be available, as is typical for proteins.

When modifying polymers, an excess of click-labeling reagent is typically used, relative to the expected degree of compound substitution. Any residual, unreacted reagent or hydrolysis product is typically removed by dialysis, chromatography or precipitation. Presence of residual, unconjugated click-labeling reagent can be detected by thin layer chromatography using a solvent that elutes the reagent away from its conjugate. In all cases it is usually preferred that the reagents be kept as concentrated as practical so as to obtain adequate rates of conjugation.

Another illustrative aspect of the present invention provides a method of click-labeling a carrier molecule or solid support, said method comprising:
contacting said carrier molecule or solid support comprising a nucleophilic group X and having the formula $R^b$—X with a compound of Formula IA or a salt thereof:

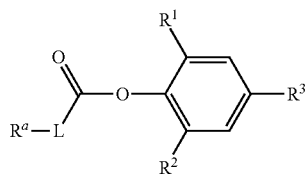

IA wherein
L is a linker,
$R^1$ is a halogen,
$R^2$ is a halogen,
$R^3$ comprises a water solubilizing group, and
$R^a$ is a click-reactive group;
and
forming a compound of Formula I or a salt thereof:

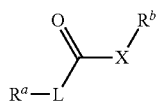

I wherein
L is the linker,
$R^a$ is the click-reactive group, and
$R^b$ is the carrier molecule or solid support comprising the nucleophilic group X.

In one particular embodiment, L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -alkoxyalkyl-, poly(alkoxyalkyl)-, PEG, -thio-, -amino-, or -substituted amino-.

In another embodiment, $R^1$ and $R^2$ are chloro.

In another embodiment, $R^3$ is —COO⁻, —SO₃⁻, substituted azenyl, PEG, phosphate, or bisphosphonate. More particularly, $R^3$ is —SO₃⁻.

In a particularly preferred embodiment, $R^1$ and $R^2$ are chloro and $R^3$ is —SO₃⁻.

In another embodiment, $R^a$ is an alkyne reactive moiety, an azide reactive moiety, a diene, a dienophile, an epoxide, or an aziridine compound. In another embodiment, the click-reactivity of $R^a$ is copper-catalyzed. In yet another embodiment, the click-reactivity of $R^a$ is not copper-catalyzed. More particularly, $R^a$ is an alkyne reactive moiety or an azide reactive moiety.

In another embodiment, the compound of Formula IA is a salt. More particularly, the salt comprises a potassium ion, a sodium ion, or a triethylammonium ion.

In another embodiment, the compound of Formula IA is soluble in an aqueous solution.

In another embodiment, the compound of Formula IA has the formula:

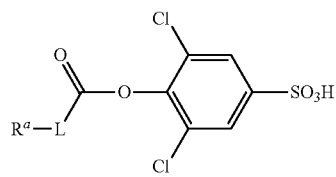

or a salt thereof, wherein
L is a linker and $R^a$ is a click-reactive group.

In another embodiment, $R^b$ is a solid support. More particularly, $R^b$ is a column or gel. Alternatively, $R^b$ is a carrier molecule. More particular still, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer. More particularly, the carrier molecule is a protein.

Another embodiment of the present invention further comprises incubating the carrier molecule or solid support with the compound of Formula IA after the contacting step.

In another embodiment, the contacting step is done in an aqueous solution.

In another embodiment, X is an amino, thio, or oxo group.

Another illustrative aspect of the present invention provides a click-labeled carrier molecule or solid support having the formula:

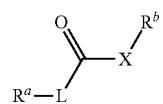

I wherein
L is a linker,
$R^a$ is a click-reactive group, and
$R^b$ is a carrier molecule or solid support comprising nucleophilic group X.

Carrier Molecules

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorophores.

Antibody binging proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCOalkyl$ and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below).

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier molecule is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., *Am. J. Physiol.*, 256: C540 (1989); and pyridyl-based and phenanthroline metal ion chelators, as described in U.S. Pat. No. 5,648,270 to Kuhn et al. (1997).

Esters of the present invention are optionally prepared in chemically reactive forms and further conjugated to polymers such as dextrans to improve their utility as sensors as described in U.S. Pat. Nos. 5,405,975 and 5,453,517.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present click-labeling reagents (compounds) are conjugated to a specific binding pair member and are used to detect an analyte in a sample. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 1.

TABLE 1

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization Solid Supports In an exemplary embodiment, the click-labeling reagents of the invention are bonded to a solid support, which includes semi-solid supports. A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include semi-solids, such as aerogels and hydrogels, resins, beads, biochips (including thin film coated biochips), multi-well plates (also referred to as microtitre plates), membranes, conducting and nonconducting metals and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. In a preferred embodiment, the solid supports contain a nucleophilic group, such as amino, thiol, or hydroxyl.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Methods of Using Click-Labeled Carrier Molecules and Solid Supports

In an exemplary embodiment, the present invention provides click-labeled carrier molecules and solid supports that may be used in a variety of click-type cycloaddition reactions.

Carrier molecules can be chemically modified, i.e., click-labeled, using the methods described herein to contain azide moieties; alkyne moieties, including but not limited to, terminal alkyne moieties; activated alkyne moieties, including, but not limited to, cyclooctyne moieties; phosphine moieties, including, but not limited to, triarylphosphine moieties; Diels Alder reactants, and epoxy or aziridine compounds with significant ring strain. These azide moieties, alkyne moieties, activated alkyne moieties, phosphine moieties, Diels Alder reactants, and epoxy or aziridine compounds are non-native, non-perturbing bioorthogonol chemical moieties that possess unique chemical functionality that can be modified through highly selective reactions. Such reactions are used in methods several of which are described herein, namely wherein the chemical modification of biomolecules that contain azide moieties or terminal alkyne moieties utilize Copper(I)-catalyzed Azide-Alkyne Cycloaddition, also referred to herein as "click chemistry"; the chemical modification of biomolecules that contain azide moieties or activated-alkyne moieties that utilize a cycloaddition reaction; and the chemical modification of biomolecules that contain azide moieties or triarylphosphine moieties utilize Staudinger ligation.

In certain embodiments, biomolecules are modified chemically by supplying cells with alkyne-containing, activated alkyne-containing, phosphine-containing, or azido-containing molecular precursors that can be incorporated into biomolecules in the cell through lipid peroxidation. In certain embodiments, biomolecules are modified by supplying cells with a terminal alkyne-containing, a cyclooctyne-containing, triarylphosphine-containing, or azido-containing molecular precursors that can be incorporated into biomolecules in the cell through lipid peroxidation.

"Click Chemistry"

Azides and terminal or internal alkynes can undergo a 1,3-dipolar cycloaddition (Huisgen cycloaddition) reaction to give a 1,2,3-triazole. However, this reaction requires long reaction times and elevated temperatures. Alternatively, azides and terminal alkynes can undergo Copper(I)-catalyzed Azide-Alkyne Cycloaddition (CuAAC) at room temperature. Such copper(I)-catalyzed azide-alkyne cycloadditions, also known as "click" chemistry, is a variant of the Huisgen 1,3-dipolar cycloaddition wherein organic azides and terminal alkynes react to give 1,4-regioisomers of 1,2,3-triazoles. Examples of "click" chemistry reactions are described by Sharpless et al. (U.S. Patent Application Publication No. 20050222427, published Oct. 6, 2005, International Application No. PCT/US03/17311; Lewis W G, et al., Angewandte Chemie-Int'l Ed. 41 (6): 1053; method reviewed in Kolb, N. C., et al., Angew. Chem. Inst. Ed. 2001, 40:2004-2021), which developed reagents that react with each other in high yield and with few side reactions in a heteroatom linkage (as opposed to carbon-carbon bonds) in order to create libraries of chemical compounds. As described herein, "click" chemistry is used in the methods for labeling modified biomolecules.

The copper used as a catalyst for the "click" chemistry reaction used in the methods described herein to conjugate a label to a modified biomolecule is in the Cu (I) reduction state. The sources of copper(I) used in such copper(I)-catalyzed azide-alkyne cycloadditions can be any cuprous salt including, but not limited to, cuprous halides such as cuprous bromide or cuprous iodide. However, this regioselective cycloaddition can also be conducted in the presence of a metal catalyst and a reducing agent. In certain embodiments, copper can be provided in the Cu (II) reduction state (for example, as a salt, such as but not limited to $Cu(NO_3)_2$ $Cu(OAc)_2$ or $CuSO_4$), in the presence of a reducing agent wherein Cu(I) is formed in situ by the reduction of Cu(II). Such reducing agents include, but are not limited to, ascorbate, tris(2-carboxyethyl) phosphine (TCEP), NADH, NADPH, thiosulfate, metallic copper, hydroquinone, vitamin $K_1$, glutathione, cysteine, 2-mercaptoethanol, dithiothreitol, $Fe^{2+}$, $Co^{2+}$, or an applied electric potential. In other embodiments, the reducing agents include metals selected from Al, Be, Co, Cr, Fe, Mg, Mn, Ni, Zn, Au, Ag, Hg, Cd, Zr, Ru, Fe, Co, Pt, Pd, Ni, Rh, and W.

The copper(I)-catalyzed azide-alkyne cycloadditions for labeling modified biomolecules can be performed in water and a variety of solvents, including mixtures of water and a variety of (partially) miscible organic solvents including alcohols, dimethyl sulfoxide (DMSO), dimethyl formamide (DMF), tert-butanol (tBuOH) and acetone.

Without limitation to any particular mechanism, copper in the Cu (I) state is a preferred catalyst for the copper(I)-catalyzed azide-alkyne cycloadditions, or "click" chemistry reactions, used in the methods described herein. Certain metal ions are unstable in aqueous solvents, by way of example, Cu(I), therefore stabilizing ligands/chelators can be used to improve the reaction. In certain embodiments at least one copper chelator is used in the methods described herein, wherein such chelators binds copper in the Cu (I) state. In certain embodiments, at least one copper chelator is used in the methods described herein, wherein such chelators binds copper in the Cu (II) state. In certain embodiments, the copper (I) chelator is a 1,10 phenanthroline-containing copper (I) chelator. Non-limiting examples of such phenanthroline-containing copper (I) chelators include, but are not limited to, bathophenanthroline disulfonic acid (4,7-diphenyl-1,10-phenanthroline disulfonic acid) and bathocuproine disulfonic acid (BCS; 2,9-dimethyl-4,7-diphenyl-1,10-phenanthroline disulfonate). In other embodiments, the copper (1) chelator is THPTA as described in Jentzsch et al., Inorganic Chemistry, 48(2): 9593-9595 (2009). In other embodiments, the copper (I) chelator are those described in Finn et al., U.S. Patent Publication No. US2010/0197871, the disclosure of which is incorporated herein by reference. Other chelators used in such methods include, but are not limited to, N-(2-acetamido) iminodiacetic acid (ADA), pyridine-2,6-dicarboxylic acid (PDA), S-carboxymethyl-L-cysteine (SCMC), trientine, tetra-ethylenepolyamine (TEPA), N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), tris-(benzyl-triazolylmethyl)amine (TBTA), or a derivative thereof. Most metal chelators, a wide variety of which are known in the chemical, biochemical, and medical arts, are known to chelate several metals, and thus metal chelators in general can be tested for their function in 1,3 cycloaddition reactions catatlyzed by copper. In certain embodiments, histidine is used as a chelator, while in other embodiments glutathione is used as a chelator and a reducing agent.

The concentration of the reducing agents used in the "click" chemistry reaction described herein can be in the micromolar to millimolar range. In certain embodiments, the concentration of the reducing agent is from about 100 micromolar to about 100 millimolar. In other embodiments, the concentration of the reducing agent is from about 10 micromolar to about 10 millimolar. In other embodiments, the concentration of the reducing agent is from about 1 micromolar to about 1 millimolar.

In certain embodiments, the methods describe herein for labeling modified biomolecules using "click" chemistry, at least one copper chelator is added after copper(II) used in the reaction has been contacted with a reducing agent. In other embodiments, at least one copper chelator can be added immediately after contacting copper(II) with a reducing agent. In other embodiments, the copper chelator(s) is added between about five seconds and about twenty-four hours after copper(II) and a reducing agent have been combined in a reaction mixture. In other embodiments, at least one copper chelator can be added any time to a reaction mixture that includes copper(II) and a reducing agent, such as, by way of example only, immediately after contacting copper(II) and a reducing agent, or within about five minutes of contacting copper(II) and a reducing agent in the reaction mixture. In some embodiments, at least one copper chelator can be added between about five seconds and about one hour, between about one minute and about thirty minutes, between about five minutes and about one hour, between about thirty minutes and about two hours, between about one hour and about twenty-four hours, between about one hour and about five hours, between about two hours and about eight hours, after copper(II) and a reducing agent have been combined for use in a reaction mixture.

In other embodiments, one or more copper chelators can be added more than once to such "click" chemistry reactions. In embodiments in which more than one copper chelators is added to a reaction, two or more of the copper chelators can bind copper in the Cu (I) state or, one or more of the copper chelators can bind copper in the Cu (I) state and one or more additional chelators can bind copper in the Cu (II) state. In certain embodiments, one or more copper chelators can be added after the initial addition of a copper chelator to the "click" chemistry reaction. In certain embodiments, the one or more copper chelators added after the initial addition of a copper chelator to the reaction can be the same or different from a copper chelator added at an earlier time to the reaction.

The concentration of a copper chelator used in the "click" chemistry reaction described herein can be determined and optimized using methods well known in the art, including those disclosed herein using "click" chemistry to label modified biomolecules followed by detecting such labeled biomolecules to determine the efficiency of the labeling reaction and the integrity of the labeled biomolecules. In certain embodiments, the chelator concentrations used in the methods described herein is in the micromolar to millimolar range, by way of example only, from 1 micromolar to 100 millimolar. In certain embodiments, the chelator concentration is from about 10 micromolar to about 10 millimolar. In other embodiments, the chelator concentration is from about 50 micromolar to about 10 millimolar. In other embodiments the chelator, can be provided in a solution that includes a water-miscible solvent such as, alcohols, dimethyl sulfoxide (DMSO), dimethyl formamide (DMF), tert-butanol (tBuOH) and acetone. In other embodiments, the chelator can be provided in a solution that includes a solvent such as, for example, dimethyl sulfoxide (DMSO) or dimethylformamide (DMF).

In certain embodiments of the methods for labeling modified biomolecules utilizing "click" chemistry described herein, the modified biomolecule can possess an azide moiety, whereupon the label possesses an alkyne moiety, whereas in other embodiments the modified biomolecule can possess an alkyne moiety, and the label possesses an azide moiety.

In certain embodiments of the methods for labeling modified biomolecules utilizing "click" chemistry described herein, the solution comprising the "click" chemistry reactants will further comprise Cu(I) ions; Cu(I) ions and a copper chelator; Cu(II) ions and at least one reducing agent; or Cu(II) ions, at least one reducing agent, and a copper chelator.

Activated Alkyne Chemistry

Azides and alkynes can undergo catalyst free [3+2] cycloaddition by a using the reaction of activated alkynes with azides. Such catalyst-free [3+2] cycloaddition can be used in methods described herein to conjugate a label to a modified biomolecule. Alkynes can be activated by ring strain such as, by way of example only, eight membered ring structures, appending electron-withdrawing groups to such alkyne rings, or alkynes can be activated by the addition of a Lewis acid such as, by way of example only, Au(I) or Au(III). Alkynes activated by ring strain have been described. For example, the cyclooctynes and difluorocyclooctynes described by Agard et al., J. Am. Chem. Soc., 2004, 126 (46):15046-15047, the dibenzocyclooctynes described by Boon et al., WO2009/067663 A1 (2009), and the aza-dibenzocyclooctynes described by Debets et al., Chem. Comm., 2010, 46:97-99.

In certain embodiments of the methods for labeling modified biomolecule utilizing activated alkynes described herein, the biomolecule can possess an azide moiety, whereupon the label possesses an activated alkyne moiety; while in other embodiments the modified biomolecule can possess an activated alkyne moiety, and the label possesses an azide moiety.

Staudinger Ligation

The Staudinger reaction, which involves reaction between trivalent phosphorous compounds and organic azides (Staudinger et al. Helv. Chim. Acta 1919, 2, 635), has been used for a multitude of applications. (Gololobov et al. Tetrahedron 1980, 37, 437); (Gololobov et al. Tetrahedron 1992, 48, 1353). There are almost no restrictions on the nature of the two reactants. The Staudinger ligation is a modification of the Staudinger reaction in which an electrophilic trap (usually a methyl ester) is placed on a triaryl phosphine. In the Staudinger ligation, the aza-ylide intermediate rearranges, in aqueous media, to produce an amide linkage and the phosphine oxide, ligating the two molecules together, whereas in the Staudinger reaction the two products are not covalently linked after hydrolysis. Such ligations have been described in U.S. Patent Application No. 20060276658. In certain embodiments, the phosphine can have a neighboring acyl group such as an ester, thioester or N-acyl imidazole (i.e. a phosphinoester, phosphinothioester, phosphinoimidazole) to trap the aza-ylide intermediate and form a stable amide bond upon hydrolysis. In certain embodiments, the phosphine can be a di- or triarylphosphine to stabilize the phosphine. The phosphines used in the Staudinger liagation methods described herein to conjugate a label to a modified biomolecule include, but are not limited to, cyclic or acyclic, halogenated, bisphosphorus, or even polymeric. Similarly, the azides can be alkyl, aryl, acyl or phosphoryl. In certain embodiments, such ligations are carried out under oxygen-free anhydrous conditions. The biomolecules described herein can be modified using a Staudinger ligation.

In certain embodiments of the methods for labeling modified biomolecules utilizing Staudinger ligation described herein, the modified biomolecule can possess an azide moiety, whereupon the label possesses a phosphine moiety, including, but not limited to, a triarylphosphine moiety; while in other embodiments the modified biomolecule can possess the phosphine moiety, and the label possesses an azide moiety.

Chemical Modification of Post Translationally Modified Biomolecules

Proteins can be modified using nucleophilic substitution reactions with amines, carboxylates or sulfhydryl groups which are found more commonly on the surface of proteins. However, the methods described herein utilize "click" reactions, cycloaddition reactions, or Staudinger ligation rather than nucleophilic substitution reactions, for selective modifications of biomolecules. Such reactions can be carried out at room temperature in aqueous conditions. In the case of "click" chemistry as described herein, excellent regioselectivity is achieved by the addition of catalytic amounts of Cu(I) salts to the reaction mixture. See, e.g., Tomoe, et al., (2002) Org. Chem. 67:3057-3064; and, Rostovtsev, et al., (2002) Angew. Chem. Int. Ed. 41:2596-2599. The resulting five-membered ring resulting from "click" chemistry cycloaddition is not generally reversible in reducing environments and is stable against hydrolysis for extended periods in aqueous environments. Thus, biomolecules attached to a labeling agent, a detection agent, a reporter molecule, a solid support or a carrier molecule via such five-membered ring are stable in reducing environments.

After biomolecules, including, but not limited to, proteins, have been modified with either azido moieties, alkyne moieties, including but not limited to, terminal alkyne moieties, such as, for example, a —C≡CH moiety; activated alkyne moieties, including, but not limited to a cyclooctyne moiety; or phosphine moieties, including, but not limited to a triarylphosphine moiety; they can be reacted under appropriate conditions to form conjugates with reporter molecules, carrier molecules or solid supports. In certain embodiments, such biomolecules used for such conjugations may be present as in a cell; as a cell lysate; as an isolated biomolecule; and/or as purified biomolecule, separated by gel electrophoresis or on a solid or semi-solid matrix.

In the methods and compositions described herein, the azide moiety may be used as the alkyne reactive group on the modified biomolecule, and an azide reactive moiety on a reporter molecule, a solid support or a carrier molecule; or the alkyne, activated alkyne or phosphine moiety may be used as the azide reactive group on the modified biomolecule, and an azide moiety may be used as an alkyne reactive moiety on a reporter molecule, a solid support or a carrier molecule. The azide reactive moiety may comprise an alkyne moiety, including, but not limited to, a terminal alkyne group, including, but not limited to, —C≡CH; an activated alkyne moiety, including, but not limited to a cyclooctyne group; or a phosphine moiety, including, but not limited to, a triarylphosphine group. In certain embodiments, the biomolecules may be modified with one or more alkyne reactive moieties, or one or more azide reactive moieties. In certain embodiments, such biomolecules are proteins.

In certain embodiments of the methods and compositions described herein, a modified protein comprising at least one azido group can be selectively labeled with a reporter molecule, a solid support and/or a carrier molecule that comprises at least one azide reactive group including, but not limited to, an alkyne group, an activated alkyne group, or a phosphine group, or a combination thereof. In other embodiments, a modified protein comprising at least one alkyne group, including, but not limited to a terminal alkyne group, such as for example, —C≡CH; an activated alkyne group, including, but not limited to, a cyclooctyne group; or a phosphine group, including, but not limited to, a triarylphosphine group, can be selectively labeled with a reporter molecule, a solid support and/or a carrier molecule that comprises at least one alkyne reactive group including, but not limited to, an azido group. In other embodiments, a modified protein comprising at least one alkyne group, including, but not limited to a terminal alkyne group, such as for example, —C≡CH; at least one activated alkyne group, including, but not limited to a cyclooctyne group; or at least one phosphine group, including, but not limited to a triarylphosphine group, can be selectively labeled with a reporter molecule, a solid support and/or a carrier molecule that comprises at least one alkyne reactive group including, but not limited to, an azido group.

In certain embodiments, two azide-reactive groups are used to label modified biomolecules: the first may be a terminal alkyne group, such as, for example, such as, for example, —C≡CH, used in a "click" chemistry reaction, and the second is a phosphine, such as a triarylphosphine group, used in a Staudinger ligation. In other embodiments, two azide-reactive groups are used to label modified biomolecules: the first may be a terminal alkyne group, such as, for example, —C≡CH, used in a "click" chemistry reaction, and the second may be an activated alkyne group, such as a cyclooctyne group, used in a cycloaddition reaction.

In certain embodiments, an alkyne reactive moiety and an azide reactive moiety are used to label modified biomolecules: the first may be an alkyne reactive moiety used in a "click" chemistry reaction, such as, for example, an azido group; and the second may be a terminal alkyne group, such as, for example, —C≡CH; an activated alkyne group, such as, for example, a cyclooctyne group, used in a cycloaddition reaction; or a phosphine group, such as, for example, a triarylphosphine group, used in a Staudinger ligation.

In one embodiment, "click" chemistry is utilized to form a conjugate with a biomolecule comprising an azido group; and a reporter molecule, solid support or carrier molecule, wherein the reporter molecule, solid support and carrier molecule comprises an alkyne group, such as, for example, a terminal alkyne group. In another embodiment, "click" chemistry is utilized to form a conjugate with a biomolecule comprising an alkyne group, such as, for example, a terminal alkyne group; and a reporter molecule, solid support and/or carrier molecule, wherein the reporter molecule, solid support and carrier molecule comprises an azido group.

In another embodiment, a cycloaddition reaction is utilized to form a conjugate with a biomolecule comprising an activated alkyne group, such as, for example, a cyclooctyne group; and a reporter molecule, solid support and/or carrier molecule, wherein the reporter molecule, solid support and carrier molecule contains an azido group.

In another embodiment, a cycloaddition reaction is utilized to form a conjugate with a biomolecule comprising an azido group, and a reporter molecule, solid support and/or carrier molecule, wherein the reporter molecule, solid support and carrier molecule comprises activated alkyne group, such as, for example, a cyclooctyne group.

In another embodiment, a Staudinger ligation is utilized to form a conjugate with a biomolecule comprising an azido group; and a reporter molecule, solid support and/or carrier molecule, wherein the reporter molecule, solid support and carrier molecule comprises a phosphine group, such as, for example, a triarylphosphine group.

In another embodiment, a Staudinger ligation is utilized to form a conjugate with a protein comprising a phosphine group, such as, for example, a triaryl phosphine group; and a reporter molecule, solid support and/or carrier molecule, wherein the reporter molecule, solid support and carrier molecule comprises an azido group.

The methods described herein are not intended to be limited to these two azide reactive groups, or chemical reactions, but it is envisioned that any chemical reaction utilizing an azide reactive group attached to a reporter molecule, solid support or carrier molecule can be used with the azide modified proteins described herein.

The reporter molecules, solid supports and carrier molecules used in the methods and compositions described herein can comprise at least one alkyne group, including, but not limited to, a terminal alkyne group; at least one activated alkyne group, including, but not limited to, a cyclooctyne group; or at least one phosphine group, including, but not limited to a triarylphosphine group; capable of reacting with an azido group of the modified biomolecule of the present invention. The reporter molecules, solid supports, and carrier molecules used in the methods and compositions described herein, can comprise at least one azide moiety capable of reacting with the alkyne group, activated alkyne group, or a phosphine group of the modified biomolecules of the present invention.

In certain embodiments, the alkyne group of the reporter molecules, solid supports, and carrier molecules described herein is a terminal alkyne group capable of reacting with the modified biomolecule of the present invention. In some embodiments, the terminal alkyne group is —C≡CH.

In certain embodiments, the activated alkyne group of the reporter molecules, solid supports, and carrier molecules described herein is a terminal alkyne group capable of reacting with the modified biomolecule of the present invention. In some embodiments, the activated alkyne group is a cyclooctyne group.

In certain embodiments, the phosphine group of the reporter molecules, solid supports, and carrier molecules described herein is a phosphine group capable of reacting with the modified biomolecule of the present invention. In some embodiments, the phosphine group is a triarylphosphine group.

In certain embodiments, the reporter molecules used in the methods and compositions described herein can include, but are not limited to labels, while the carrier molecules can include, but are not limited to, affinity tags, nucleotides, oligonucleotides and polymers. The solid supports can include, but are not limited to, solid support resins, microtiter plates and microarray slides.

Sample Preparation:

The end user will determine the choice of the sample and the way in which the sample is prepared. The sample includes, without limitation, any material for labeling which contains a nucleophile amenable to reaction with the click-labeling reagents of the present invention. Preferably the material is biologically-derived or a synthetic macromolecule.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, β cells, hepatocytes, and neurons.

In many instances, it may be advantageous to add a small amount of a non-ionic detergent to the sample. Generally the detergent will be present in from about 0.01 to 0.1 vol. %. Illustrative non-ionic detergents include the polyoxyalkylene diols, e.g. Pluronics, Tweens, Triton X-100, etc.

Kits

Additional embodiments of the present invention include kits comprising the click-labeling reagents described herein for use in labeling carrier molecules or solid supports. In addition to the compounds, the kits include instructions on how to reporter molecule the carrier molecule or solid support. One particular embodiment provides a kit for forming a conjugate with a carrier molecule or solid support and a click-labeling reagent, wherein the kit comprises:

a) a compound of Formula IA or a salt thereof:

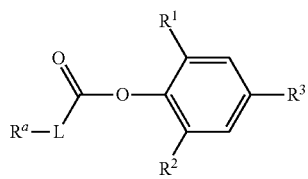

IA wherein
L is a linker,
$R^1$ is a halogen,
$R^2$ is a halogen,
$R^3$ comprises a water solubilizing group, and
$R^a$ is a click-reactive group;
and b) instructions for click-labeling the carrier molecule or solid support.

In one embodiment, L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -alkoxyalkyl-, poly(alkoxyalkyl)-, PEG, -thio-, -amino-, or -substituted amino-. More particular still, L is single a covalent bond. Alternatively, L is -alkyl- or -substituted alkyl-; more particularly -pentyl- or -polyethylglycol- or -amino-dPEG$_4$- acid. Alternatively, L is -substituted heterocyclyl-; more particularly, -piperidine-1-carbonyl-.

In another embodiment, $R^1$ and $R^2$ are chloro. In another embodiment, $R^1$ and $R^2$ are fluoro.

In another embodiment, $R^3$ is —COO$^-$, —SO$_3^-$, substituted azenyl, PEG, phosphate, or bisphosphonate. More particularly, $R^3$ is —SO$_3^-$.

In a particularly preferred embodiment, $R^1$ and $R^2$ are chloro and $R^3$ is —SO$_3^-$.

In another embodiment, $R^a$ is an alkyne reactive moiety, an azide reactive moiety, a diene, a dienophile, an epoxide, or an aziridine compound. In another embodiment, the click-reactivity of $R^a$ is copper-catalyzed. In yet another embodiment, the click-reactivity of $R^a$ is not copper-catalyzed. More particularly, $R^a$ is an alkyne reactive moiety or an azide reactive moiety.

In another embodiment, the compound of Formula IA is a salt. More particularly, the salt comprises a potassium ion, a sodium ion, or a triethylammonium ion.

In another embodiment, the compound of Formula IA is soluble in an aqueous solution.

In another embodiment, the compound of Formula IA has the formula:

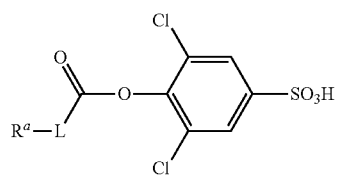

or salt thereof,
wherein
L is a linker and $R^a$ is a click-reactive group.

Various ancillary materials will frequently be employed in an assay in accordance with the present invention. In an exemplary embodiment, buffers and/or stabilizers are present in the kit components. In another exemplary embodiment, the kits comprise indicator solutions or indicator "dipsticks", blotters, culture media, cuvettes, and the like. In yet another exemplary embodiment, the kits comprise indicator cartridges (where a kit component is bound to a solid support) for use in an automated detector. In another exemplary embodiment, the kit further comprises molecular weight markers, wherein said markers are selected from phosphorylated and non-phosphorylated polypeptides, calcium-binding and non-calcium binding polypeptides, sulfonated and non-sulfonated polypeptides, and sialylated and non-sialylated polypeptides. In another exemplary embodiment, the kit further comprises a member selected from a fixing solution, a detection reagent, a standard, a wash solution, and combinations thereof.

A detailed description of the invention having been provided above, the following examples are given for the purpose of illustrating the invention and shall not be construed as being a limitation on the scope of the invention or claims.

EXAMPLES

Example 1

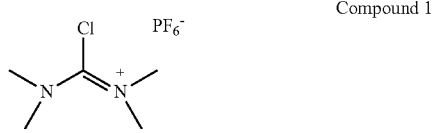

Compound 1

To a solution of 1,1,3,3-tetramethylurea (2.5 mL, 21 mmol) in 10 mL of toluene was added oxalyl chloride (2.0 mL, 23 mmol) in a small portion over 2 min. period while the reaction mixture was stirred at an ice-water bath temperature. After stirring at room temperature 18 hr, the reaction mixture was concentrated to a volume of about 5 mL under reduced pressure and the resulting precipitate was collected by filtration. The collected solid was dissolved in about 20 mL of water followed by treating with a solution of potassium hexafluorophosphate (3.8 g, 21 mmol) in 50 mL of water while the mixture was stirred vigorously at room temperature to give a white precipitate. The precipitate was collected by filtration and dried under vacuum. The solid was then treated with about 8 mL of acetone and filtered to remove insoluble material. The resulting filtrate was added in a small portion into 60 mL of ether while stirring vigorously at room temperature.

The desired product was collected by filtration and dried under vacuum to give 4.5 g (76%) as a white solid.

Example 2

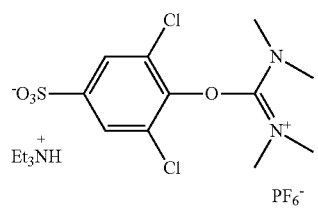

Compound 2

To a solution of 3,5-dichloro-4-hydroxybenzenesulfonic acid (2.9 g, 8.2 mmol) in 35 mL of acetonitrile was added [chloro(dimethylamino)methylene]dimethylammonium hexafluorophosphate (3.2 g, 11 mmol). It was then added triethylamine (3.4 mL, 25 mmol) in a small portion over 5 min. while the mixture was stirred at an ice-water bath temperature. After stirring for 30 min, the resulting precipitate was filtered and the filter cake was washed with about 10 mL of acetonitrile. The combined filtrate was concentrated under reduced pressure to give a crude product. The crude product was purified by column chromatography on silica gel (eluant, $H_2O:CH_3CN$, 2:98 to 7:97) to give 2.6 g (53%) of the desired product as a white solid. TLC: $R_f$=0.41 (silica gel, 15% $H_2O$ in $CH_3CN$).

Example 3

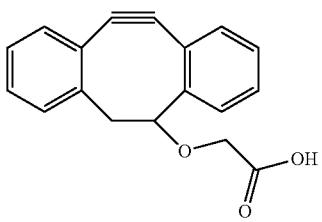

Compound 3

To a solution of 5,6-dihydro-11,12-didehydro-dibenzo[a,e]cycloocten-5-ol (1.6 g, 7.3 mmol, Boons et. al. *Angew. Chem. Int Ed.* 47, 2253-2255, 2008) in 30 mL of dry THF was added sodium hydride (60% dispersed in mineral oil, 1.1 g, 28 mmol) in a small portion over 5 min period while the reaction mixture was stirred at room temperature. After stirring for 30 min. ethyl bromoacetate (2.0 mL, 18 mmol) was added in one portion and the whole reaction mixture was stirred at room temperature under $N_2$ atmosphere for 5 hr. To the reaction mixture was added 20 mL of an aqueous solution of 1 M NaOH slowly over 5 min. period while stirring at room temperature. It was then added 20 mL of methanol and the reaction mixture was stirred at 50° C. for 3 hrs. After the reaction mixture was cooled down to room temperature, 20 mL of water was added. The pH of the reaction mixture was adjusted to pH 3 by the addition of 10 mL aqueous solution of 3 M HCl in a small portion over 5 min. period while stirring at room temperature. It was then extracted with chloroform (2×75 mL) followed by drying of the organic phase with anhydrous sodium sulfate and concentration under reduced pressure to give a crude product. It was purified by column chromatography over silica gel (eluant, 5% methanol in chloroform) to give 1.5 g (73%) of the desired product as a white solid. TLC: $R_f$=0.32 (silica gel, 15% methanol in chloroform), Absorption max.: 290 nm, 304 nm in methanol.

Example 4

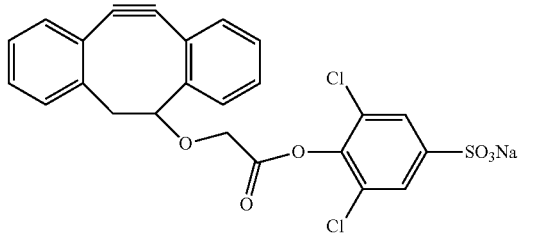

Compound 4

To a solution of Compound 3 (0.60 g, 2.2 mmol) and DMAP (0.26 g, 2.2 mmol) in 30 mL of dry DMF was added Compound 2 (1.52 g, 2.6 mmol) and the mixture was stirred at room temperature for 16 hrs. The reaction mixture was concentrated under vacuum to remove DMF and the resulting crude product was purified by column chromatography over silica gel (eluant, methanol/chloroform (5:95 to 12:88)) to give a white solid. It was dissolved in 20 mL of water/methanol (1:1) and treated with 50 mL of Dowex 50WX2-200H Na form to obtain the desired product as a sodium form (0.97 g, 85%). TLC: $R_f$=0.73 (25% methanol in chloroform), Absorption max.: 290 nm and 304 nm in methanol.

Example 5

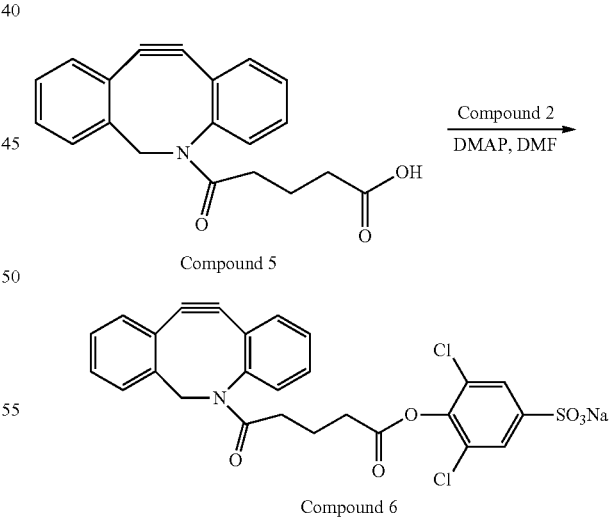

The Compound 6 is prepared in a similar manner as described in Example 4 from Compound 5 (1.0 mmol, van Delft et. al. *Chem. Commun.* 46, 97-99, 2010), DMAP (1.0 mmol) and Compound 2. After purification and salt exchange, the desired product is obtained as a white solid.

Example 6

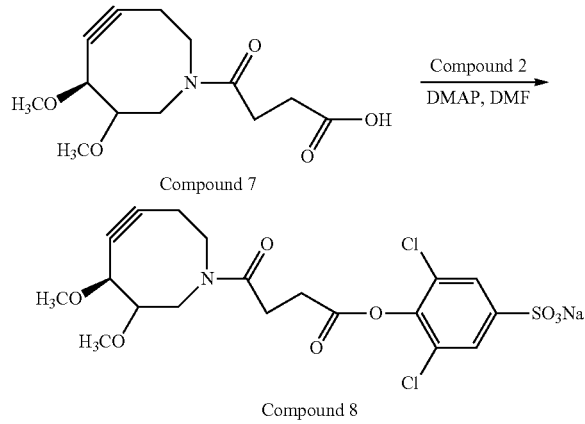

The Compound 8 is prepared in a similar manner as described in Example 4 from Compound 7 (1.0 mmol, Bertozzi et. al. *Organic Letters* 10, 3097-3099, 2008), DMAP (1.0 mmol) and Compound 2 (1.5 mmol) in 15 mL of dry DMF. After purification and salt exchange, the desired product is obtained as a white solid.

Example 7

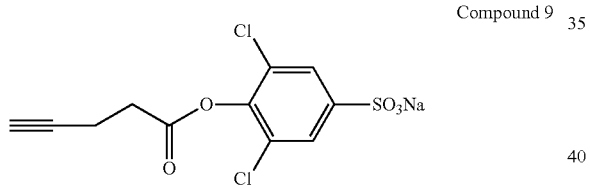

The Compound 9 is prepared in a similar manner as described in Example 4 from 4-pentynoic acid (1.0 mmol), DMAP (1.0 mmol) and Compound 2 (1.5 mmol) in 15 mL of dry DMF. After purification and salt exchange, the desired product is obtained as a white solid.

Example 8

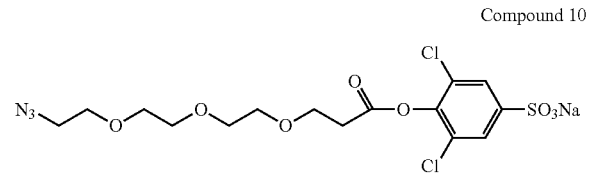

The Compound 10 is prepared in a similar manner as described in Example 4 from 12-azido-4,7,10-trioxadodecanoic acid (1.0 mmol), DMAP (1.0 mmol) and Compound 2 (1.5 mmol) in 15 mL of dry DMF. After purification and salt exchange, the desired product is obtained as a white solid.

Example 9

Qdot®605-DIBO Conjugate

A solution (7 µL) of Compound 4 (10 mg/mL in DMSO) was added into a solution (120 µL) of Qdot®605 AMP-PEG2K-100N (8.4 µM in 50 mM borate buffer, pH 8.3) while being stirred at room temperature. After the reaction mixture was stirred at room temperature for 1 hr, the Qdot®605-DIBO conjugate was separated from the free unreacted reagent by passing through a BioGel P-30 (medium resin) desalting column eluting with PBS buffer, pH 7.3. The obtained desired Qdot®605-DIBO conjugate (10 µL) was clicked to Alexa Fluor 647 azide (6 µL, 1 mg/mL) by stirring at room temperature overnight. The degree of labeling (DOL) was estimated by size-exclusion (SEC) HPLC analysis. The DOL of 1.26 was estimated by height ratio between the peaks at 650 nm and 600 nm from the absorption spectrum.

Example 10

Chemical (SDP-$N_3$) Click Tagging of Antibody

Chemical click-labeling via SDP-$N_3$ was used to label amine side chains of Lys residues in anti-GFP antibody; labeling is not chain specific and is dictated by the frequency of Lys residues. SDP-$N_3$-modified antibody+DIBO-converted oligonucleotide results are shown in FIG. 3.

Each of the above-cited references is hereby incorporated by reference as if set forth fully herein.

The invention claimed is:

1. A compound of Formula IA or a salt thereof:

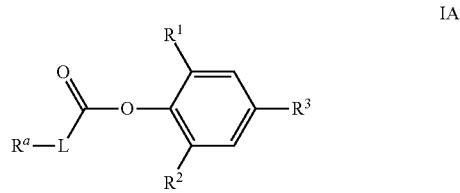

wherein
L is a linker,
$R^1$ is a halogen,
$R^2$ is a halogen,
$R^3$ comprises a water solubilizing group, and
$R^a$ is a click-reactive group selected from the group consisting of an alkyne reactive moiety, an azide reactive moiety, a diene, a dienophile, an epoxide or an aziridine compound.

2. The compound of claim 1, where the click-reactivity of $R^a$ is copper-catalyzed.

3. The compound of claim 1, where the click-reactivity of $R^a$ is not copper-catalyzed.

4. The compound of claim 1, wherein L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloalkyl-, -substituted cycloalkyl-, -oxy-, -alkoxy-, -substituted alkoxy-, -alkoxyalkyl-, poly(alkoxyalkyl)-, PEG, -thio-, -amino-, or -substituted amino-.

5. The compound of claim 1, wherein $R^1$ and $R^2$ are chloro.

6. The compound of claim 1, wherein $R^3$ is —COO⁻, —$SO_3^-$, substituted azenyl, PEG, phosphate, or bisphosphonate.

7. The compound of claim 5, wherein $R^3$ is —$SO_3^-$.

8. The compound of claim 1, wherein the compound of Formula IA is a salt.

9. The compound of claim 8, wherein the salt comprises a potassium ion, a sodium ion, or a triethylammonium ion.

10. The compound of claim 1, wherein $R^a$ is an alkyne reactive moiety or an azide reactive moiety.

11. The compound of claim 7, wherein $R^a$ is an alkyne reactive moiety or an azide reactive moiety.

12. The compound of claim 11, where the compound has the formula comprising:

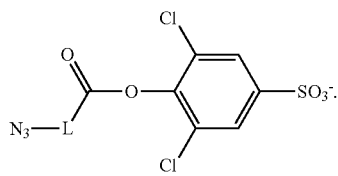

13. The compound of claim 11, where the compound has the formula comprising:

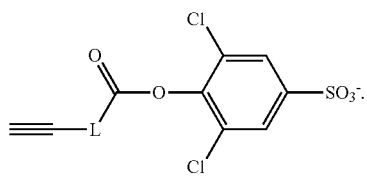

14. The compound of claim 11, where the compound has the formula comprising:

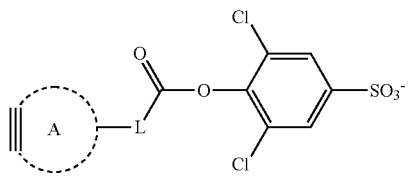

wherein A is a substituted or unsubstituted cyclooctyne ring that may contain a heteroatom and/or be fused to one or more 5- or 6-membered aromatic or heteroaromatic rings.

15. The compound of claim 12, wherein the compound is

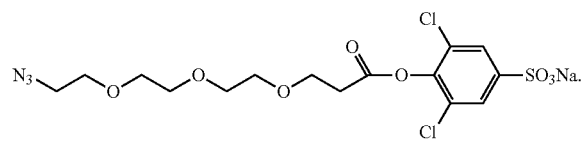

16. The compound of claim 13, wherein the compound is

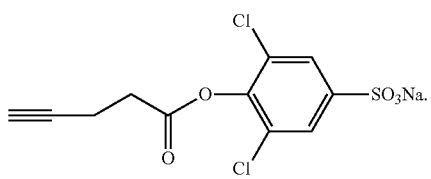

17. The compound of claim 14, wherein the compound is selected from the group consisting of:

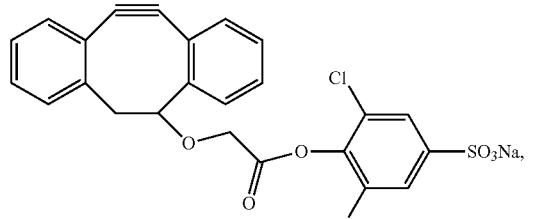

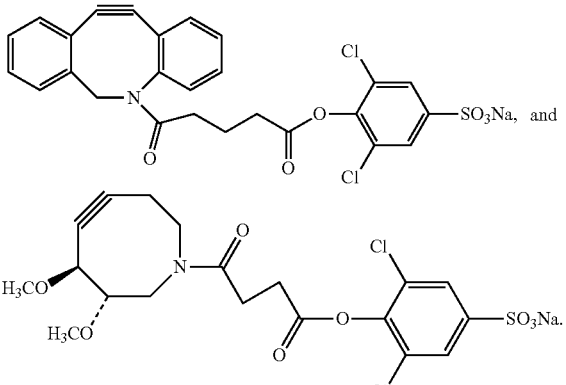

18. A method of click-labeling a carrier molecule or solid support, said method comprising:
contacting said carrier molecule or solid support comprising a nucleophilic group X and having the formula $R^b$—X with a compound of Formula IA or a salt thereof:

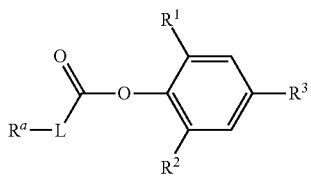

wherein
L is a linker,
$R^1$ is a halogen,
$R^2$ is a halogen,
$R^3$ comprises a water solubilizing group, and
$R^a$ is a click-reactive group selected from the group consisting of an alkyne reactive moiety, an azide reactive moiety, a diene, a dienophile, an epoxide or an aziridine compound;
and
forming a compound of Formula I or a salt thereof:

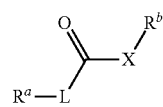

wherein
L is the linker,
$R^a$ is the click-reactive group, and
$R^b$ is the carrier molecule or solid support comprising the nucleophilic group X.

19. A click-labeled carrier molecule prepared by the method of claim 18.

* * * * *